(12) United States Patent
Oran

(10) Patent No.: US 11,892,460 B2
(45) Date of Patent: Feb. 6, 2024

(54) METHOD FOR EXTRACTION AND DETERMINATION OF FATTY ACID IN BIOLOGICAL FLUID

(71) Applicant: Ismail Oran, Izmir (TR)

(72) Inventor: Ismail Oran, Izmir (TR)

( * ) Notice: Subject to any disclaimer, the term of this patent is extended or adjusted under 35 U.S.C. 154(b) by 751 days.

(21) Appl. No.: 17/056,009

(22) PCT Filed: May 7, 2019

(86) PCT No.: PCT/TR2019/050301
§ 371 (c)(1),
(2) Date: Nov. 17, 2020

(87) PCT Pub. No.: WO2019/245507
PCT Pub. Date: Dec. 26, 2019

(65) Prior Publication Data
US 2021/0255208 A1    Aug. 19, 2021

(30) Foreign Application Priority Data
May 17, 2018    (TR) ............................. TR2018/06990

(51) Int. Cl.
*G01N 33/92*    (2006.01)
(52) U.S. Cl.
CPC .................... *G01N 33/92* (2013.01)
(58) Field of Classification Search
CPC ..................................................... G01N 33/92
See application file for complete search history.

(56) References Cited

U.S. PATENT DOCUMENTS

| 4,369,250 | A | 1/1983 | Gindler |
| 6,750,030 | B2 | 6/2004 | Kleinfeld |
| 9,354,222 | B2 | 5/2016 | Jung et al. |
| 2002/0160537 | A1 | 10/2002 | Kleinfeld et al. |
| 2008/0305550 | A1 | 12/2008 | Huff et al. |
| 2010/0291611 | A1 | 11/2010 | Bolbot et al. |
| 2011/0045520 | A1 | 2/2011 | Bhagavan et al. |

FOREIGN PATENT DOCUMENTS

WO    2017116358 A1    7/2017

OTHER PUBLICATIONS

Ismail Oran et al., Ischemia-Modified Albumin as a Marker of Acute Coronary Syndrome: The Case for Revising the Concept of "N-Terminal Modification" to "Fatty Acid Occupation" of Albumin, Disease Markers, 2017, pp. 1-8.
Lionel H. Opie, Metabolism of Free Fatty Acids, Glucose and Catecholamines in Acute Myocardial Infarction: Relation to Myocardial Ischemia and Infarct Size, The American Journal of Cardiology, Dec. 1975, pp. 938-953, vol. 36, 7.
Alan M. Kleinfeld et al., Serum Levels of Unbound Free Fatty Acids Reveal High Sensitivity for Early Detection of Acute Myocardial Infarction in Patient Samples From the TIMI II Trial, Journal of American Collage of Cardiology, 2002, 39, 312A.
Fred S. Apple et al., Unbound Free Fatty Acid Concentrations Are Increased in Cardiac Ischemia, Clinical Proteomics Journal, 2004, pp. 41-44, vol. 1.
Vijay Kumar Roy et al., Plasma Free Fatty Acid Concentrations as a Marker for Acute Myocardial Infarction, Journal of Clinical and Diagnostic Research, 2013, pp. 2432-2434, vol. 7(11).
Andrew H. Huber et al., Usefulness of Serum Unbound Free Fatty Acid Levels to Predict Death Early in Patients with ST Segment Elevation Myocardial Infarction (from the Thrombolysis In Myocardial Infarction [TIMI] II Trial), Journal of American Collage of Cardiology, 2014, pp. 279-284, vol. 113, Issue 2.
Michael F Oliver, Fatty acids and the risk of death during acute myocardial ischaemia, Clinical Science, 2015, pp. 349-355, 128(6).
Alan M. Kleinfeld et al., Increases in Serum Unbound Free Fatty Acid Levels Following Coronary Angioplasty, The American Journal of Cardiology, 1996, pp. 1350-1354, vol. 78.
Anju Bhardwaj et al., A multicenter comparison of established and emerging cardiac biomarkers for the diagnostic evaluation of chest pain in the emergency department, American Heart Journal, 2011, pp. 276-282, vol. 162, No. 2.
Raymond F. Chen, Removal of Fatty Acids from Serum Albumin by Charcoal Treatment, The Journal of Biological Chemistry, 1967, pp. 173-181, vol. 242, No. 2.
Naomi I. Nakano et al., Activated Carbon Beads For The Removal off Highly Albumin-Bound Species, Analytical Biochemistry, 1983, pp. 64-71, vol. 129, Issue 1.
Wojciech Bal et al., Binding of transition metal ions to albumin: Sites, affinities and rates, Biochimica et Biophysica Acta (BBA)—General Subjects, 2013, pp. 1-12.

*Primary Examiner* — Samuel P Siefke
(74) *Attorney, Agent, or Firm* — Bayramoglu Law Offices LLC

(57) ABSTRACT

A method for determining fatty acid level in case of acute or chronic medical conditions, and diagnosing medical conditions associated with increased fatty acid level in a biological sample containing albumin is provided. The method includes incubation of patient's sample and high surface area carbon-based electrode together in a holder. Due to attractive hydrophobic interaction between the albumin's surface fatty acids and the carbon-based material, the electrode self-extracts fatty acids from the albumin. The method eventually includes adsorption/accumulation with subsequent monolayer formation of extracted fatty acids over the carbon-based electrode. Accumulation of the fatty acid monolayer changes already existing electrode-electrolyte (sample) interfacial construct, which in turn changes also the interfacial states, such as electrical double layer capacitance. The appropriate electrical/electrochemical measurement reflects the magnitude of extracted fatty acids from the albumin that is indicative of acute or chronic medical conditions.

1 Claim, No Drawings

METHOD FOR EXTRACTION AND DETERMINATION OF FATTY ACID IN BIOLOGICAL FLUID

CROSS REFERENCE TO THE RELATED APPLICATIONS

This application is the national phase entry of International Application No. PCT/TR2019/050301, filed on May 7, 2019, which is based upon and claims priority to Turkish Patent Application No. 2018/06990, filed on May 17, 2018, the entire contents of which are incorporated herein by reference.

TECHNICAL FIELD

This invention is related to the method ensuring diagnosis of acute or chronic pathologic (abnormal) medical conditions associated with altered fatty acid metabolism by extracting fatty acids from the albumin and concomitantly detecting fatty acids in serum, plasma, whole blood, or any body fluids in a patient. More specifically, the described method is useful for diagnosis as well as prognosis and follow-up of acute myocardial ischemia.

BACKGROUND

Well-known biochemical markers of myocardial ischemia include creatine kinases, troponins, myoglobin, and fatty acid binding protein that are released from cells following cell membrane damage, usually 4-6 hours later after beginning of the chest pain. Another important disadvantage of these markers is that they give non-specific results in case of angina pectoris not accompanying myocardial cell damage. There is an emerging need for early and specific markers that would be positive immediately after (within minutes) the beginning of ischemia (before cell death), to allow treatment of the disease prior to irreversible damage. One such marker is FDA-approved ischemia modified albumin (IMA) that is diagnosed by albumin-cobalt binding (ACB) test. It has been proposed as exclusion test for acute myocardial ischemia in emergency setting [patent no: U.S. Pat. No. 5,227,307 (Bar-Or et al.), no: U.S. Pat. No. 5,290,519 (Bar-Or et al.), application publication no: US 2005/0021235 (Bar-Or et al.)]. The ACB test, however, has not gained expected clinical impact for more than a decade due mainly to low accuracy. We now know that, contrary to the original description by Bar-Or, IMA is actually "fatty acid occupied albumin" along with the well-known rapid increase of blood fatty acids in case of acute myocardial ischemia (Oran I, Ischemia-modified albumin as a marker of acute coronary syndrome: The case for revising the concept of "N-terminal modification" to "fatty acid occupation" of albumin. Disease Markers 2017, Article ID 5692583).

Human serum contains a mixture of 20 more fatty acids (FAs); oleic, palmitic, linoleic, stearic, arachidonic and linolenic acids together constitute more than 95% of all FAs. Human serum albumin has at least 7 binding sites with varying affinities for medium and long chain FAs (Petitpas, I et al. Crystal structures of human serum albumin complexed with monounsaturated and polyunsaturated fatty acids, J. Mol. Biol. 2001; 314: 955-960; Simard J R, et al. Location of high and low affinity fatty acid binding sites on human serum albumin revealed by NMR drug-competition analysis. J Mol Biol 2006; 361: 336-351). Under normal physiologic condition, 0.2-1.5 molecules of FAs are bound to each albumin molecule (Brodersen, R., et al. Multiple fatty acid binding to albumin in human blood plasma. Eur. J. Biochem. 1990; 189:343-349; Huber A H, Kleinfeld A M. Unbound free fatty acid profiles in human plasma and the unexpected absence of unbound palmitoleate. J Lipid Res, 2017; 58:578-585). Nearly all released blood FAs are tightly bound to albumin immediately and transported throughout the body while a very small percentage (less than 1/100,000) is present in unbound form (so-called unbound or free FA), which is in the nM (nanomolar) range (Richieri G V, Kleinfeld A M. Unbound free fatty acid levels in human serum. J Lipid Res. 1995; 36: 229-240; Huber A H, Kleinfeld A M. Unbound free fatty acid profiles in human plasma and the unexpected absence of unbound palmitoleate. J Lipid Res, 2017; 58:578-585).

Myocardial ischemia causes a hyperadrenergic state which results in breakdown of tissue and plasma phospholipids and triglycerides with resultant increased plasma concentration of FAs within minutes after beginning of chest pain. Bound (to albumin) FA level (usually depicted as non-esterified fatty acid-NEFA) in myocardial ischemia increases as expected, which is generally higher than 1-1.2 mM (millimolar) in clinical settings (Bhagavan N V, et al. Utility of serum fatty acid concentrations as a marker for acute myocardial infarction and their potential role in the formation of ischemia-modified albumin: A pilot study. Clin Chem, 2009; 55:1588-1590; Oliver M F. Fatty acids and the risk of death during acute myocardial ischemia. Clin Science 2015; 128:349-355). In general, FA/albumin molar ratio of 4 reflects the corresponding free (unbound) FA level of less than 50 nM (physiologic level is less than 5 nM). Free FA level increases exponentially above the molar ratio of 4, then become saturated at 6-7. When the pH of medium is lowered, the total free (unbound) FA level increases (Spector A A, et al. Binding of long-chain fatty acids to bovine serum albumin. J Lipid Res, 1969; 10:56-67; Huber A H, et al. Fatty acid-specific fluorescent probes and their use in resolving mixtures of unbound free fatty acids in equilibrium with albumin. Biochemistry, 2006; 45:14263-14274; Huber A H, et al. Unbound free fatty acid profiles in human plasma and the unexpected absence of unbound palmitoleate. J Lipid Res, 2017; 58:578-585).

In particular, patients with acutely ischemic myocardium exhibit a rapid increase in serum free FA levels also; it can exceed normal average values by as much as 3-10 folds (Opie L H. Metabolism of free fatty acids, glucose and catecholamines in acute myocardial infarction. Am J Cardiol, 1975; 36:938-953; Kleinfeld A M, et al. Serum levels of unbound free fatty acids reveal high sensitivity for early detection of acute myocardial infarction in patient samples from the TIMI II trial. J Am Coll Cardiol, 2002; 39:312A; Apple F S, et al. Unbound free fatty acid concentrations are increased in cardiac ischemia. Clinical Proteomics, 2004; 1:41-44; Roy V K, et al. Plasma free fatty acid concentrations as a marker for acute myocardial infarction. J Clin Diag Res, 2013; 7:2432-2434; Huber A H, et al. Usefulness of serum unbound free fatty acid levels to predict death early in patients with ST-segment elevation myocardial infarction (from the Thrombolysis in Myocardial Infarction [TIMI] II trial). Am J Cardiol, 2014; 113:279-284; Oliver M F. Fatty acids and the risk of death during acute myocardial ischaemia. Clin Science, 2015; 128:349-355). Serum levels of free FAs have also been reported to increase within 30 minutes of coronary balloon angioplasty (a well-known in vivo model for transient myocardial ischemia caused by balloon inflation) and a mean 5-fold increase in free FA levels has been reported (Kleinfeld A M, et al. Increases in serum unbound free fatty acid levels following coronary angioplasty. Am J Cardiol, 1996; 78: 1350-1354).

A recent multicenter study investigated the utility of measuring level of free FAs compared with other available clinical tests (i.e., amino terminal pro-B-type natriuretic peptide, IMA, heart fatty acid binding protein, classical troponin T, and high-sensitive troponin I) and found that free FA had the highest overall sensitivity (75%), specificity (72%), and negative predictive values (92%) for discriminating acute coronary syndrome from nonischemic chest pain in patients admitted to the emergency department (Bhardwaj A, et al. A multicenter comparison of established and emerging cardiac biomarkers for the diagnostic evaluation of chest pain in the emergency department. Am Heart J, 2011; 162:276-282). Thus, current data suggest that monitoring of level of FAs in patients presenting with chest pain may provide an early indicator of myocardial ischemia that is able to discriminate between acute coronary syndrome and nonischemic chest pain.

The patent no: U.S. Pat. No. 6,750,030 (Kleinfeld et al.) and patent application publication no: US 2011/0045520 (Bhagavan et al.) disclosed usage of free FA level as a biochemical marker of acute myocardial ischemia, since they found 2-fold and 5-fold increased free FA levels in their patients' blood respectively although their measurement methods are different. The patent application publication no: US 2008/0305550 (Huff et al.) also disclosed a method of determining the ischemic event by determining the amount of FA that is complexed to albumin. The patent application publication no: WO 2017/116358 (Oran I) disclosed a method of determining the free FAs level in a patient's sample by using specific electrochemical redox reaction, namely anodic decarboxylation (Kolbe) reaction. The patent no: U.S. Pat. No. 9,354,222 (Jung B H et al.) disclosed usage of serum profile of multiple lysophosphatidylcholine and FA molecules as a marker of acute myocardial ischemia. None of above-mentioned patents have disclosed the method described here.

Carbon-based materials (in short, "carbon"), which come from organic parent source with different carbonization and manufacturing processes, have a typical hexagonal carbon backbone. Single atomic layer hexagonal carbon backbone is called graphene, while multiple stuck graphene layers compose graphite bulk. It has long been known that ionic surfactants such as FAs (monocarboxylic acid with medium and long hydrocarbon chain) adsorb with two-step process from aqueous solution onto the hydrophobic surface of carbon-based materials. In the first adsorption step, at low surfactant concentration, the surfactant molecules self-assemble horizontally on the carbon plane. While approaching higher concentration as much as critical micelle concentration, in the second step, surface hemi micelles are formed by the excess surfactant molecules. The major driving force of this high-affinity adsorption process is the strong hydrophobic interaction between the surfactant's long hydrophobic hydrocarbon chain and the hydrophobic carbon surface. There is nearly perfect matching of the alkyl skeleton of surfactant molecule in a zigzag conformation with the hexagonal carbon backbone, which favors energetically epitaxial ordering. Since the adsorption kinetic is mainly favored by the hydrophobic interaction, the adsorption force/amount is higher for longer chain surfactants and for carbon surface having less oxygen functional groups (carbon surface having more oxygen functional groups-oxidized carbon-becomes hydrophilic). The adsorption is also favored by lower solution pH. (Chudoba J, et al. A study on lower fatty acids and polyethylene glycols adsorption on activated carbon. Acta Hydrocim Hydrobiol, 1978; 6:153-158; Hibino M, et al. Scanning tunneling microscopy study on dynamic structural formation in mixed fatty-acid monolayers at liquid/graphite interface. Thin Solid Films, 1996; 281-282:594-597; Kiraly Z et al. Adsorption calorimetric study of the organization of sodium n-decyl sulfate at the graphite/solution interface. Langmuir 2001; 17:2420-2425; Hua Wu S, et al. Adsorption of anionic surfactant by activated carbon: Effect of surface chemistry, ionic strength, and hydrophobicity. J Colloid Interface Sci, 2001; 243:306-315; Bickerstaffe A K, et al. The crystalline structures of carboxylic acid monolayers adsorbed on graphite. J Phys Chem B, 2006; 110:5570-5575; Radic S, et al. Competitive binding of natural amphiphiles with graphene derivatives. Sci Reports, 2013; 3:2273; Medina S, et al. Monolayer arrangement of fatty hydroxystearic acids on graphite: Influence of hydroxyl groups. Thin Solid Films 2013; 539:194-200; Yang T, et al. Self assembly of long chain alkanes and their derivatives on graphite. J Chem Physics, 2008; 128: 124709).

Commercially available albumin preparations have usually FA impurities; however, some laboratory experiments necessitate purified (de-fatted) albumin. Removal of FAs from albumin surface which was described by Chen 50 years ago, is based on the treatment of sample with charcoal (activated carbon) at low (usually 3) pH. This treatment results in extraction of FAs from the albumin with subsequent adsorption/accumulation on the carbon surface which follows Freundlich adsorption kinetics. Nearly complete removal is usually accomplished within 10 minutes for most FAs at ideal conditions. De-fatting down to FA/albumin molar ratio of 1.5 (upper limit of physiologic FAs level) can be obtained even in neutral pH. Electrolyte pH, contact time and carbon surface area are three main determinants of efficiency of de-fatting process (Chen R F. Removal fatty acids from serum albumin by charcoal treatment. J Biol Chem, 1967; 25:173-181; Nakano N I, et al. Activated carbon beads for the removal of highly albumin-bound species. Analytic Biochem, 1983; 129:64-71).

The electrode-electrolyte interface constructs an electrical double layer that behaves as a capacitor where accumulation and buildup of array of charges (i.e., ions with hydration shell) occurs. There exists a thin layer of dielectric molecules (i.e., water) at the interface between electrode-electrolyte and at the interface between individual arrays of charges in electrolyte, which both exert an influence on the total capacitance of the electrode in the electrolyte (Jiang G, et al. Molecular dynamics simulations of the electric double layer capacitance of graphene electrodes in mono-valent aqueous electrolytes. Nano Research, 2016; 9:174-186). While the adsorption of larger organic molecules on the electrode surface, the dielectric thin layer and closest array of charged particles move away from the electrode surface, which results in decreasing the so-called double layer capacitance. Since there is no electron transfer (no redox reaction) between electrolyte and electrode, the double layer capacitance is highly sensitive to interfacial (between electrode-electrolyte) adsorption event of organic molecules. The determination of any analyte adsorbed on the electrode by using measurement of double layer capacitance is also called capacitive biosensing (Berggren C. Capacitive biosensors. Electroanalysis, 2001; 13:173-180; Tsouti V, et al. Capacitive microsystems for biological sensing. Biosensors Bioelectronics, 2011; 27:1-11; Wongkittisuksa B, et al. Development and application of a real-time capacitive sensor. Biosensors Bioelectronics, 2011; 26:2466-2472). Carbon-based electrode materials have been widely used in both analytical and industrial electrochemistry for many years. The advantages of carbon electrodes include low cost, wide potential window, relative inert electrochemistry, and electrocatalytic activity for a variety of redox reactions (McCreery R L. Advanced carbon electrode materials for molecular electrochemistry. Chem Rev, 2008; 108:2646-2687).

SUMMARY

It is an object of the present invention to provide a diagnostic test method that detects a change in FA composition of the patient's fluidic sample which also contains albumin.

It is another object of the present invention to provide a diagnostic test method that has at least two electrodes dipped into the patient's fluidic sample, wherein one of these electrodes is composed of carbon-based materials.

Another object is to provide a diagnostic test method that provides sufficient incubation time, wherein most (if not all) of the sample's albumin molecules have enough time for face off carbon-based electrode surface.

Another object is to provide a diagnostic test method that provides relatively high electrode surface area, wherein the carbon-based electrode surface is in contact widely with the patient's fluidic sample which allows the functioning of hydrophobic attraction force between albumin's FAs and carbon-based material of the electrode.

Another object is to provide a diagnostic test method that allows eventually self-extraction of FAs from the sample's albumin surface with concomitant adsorption of extracted FAs on the carbon-based electrode.

It is another object of the present invention to provide a diagnostic test method that detects FAs on the carbon-based electrode surface, wherein adsorbed FAs make changes electrical/electrochemical response of electrode (carbon-based material)-electrolyte (patient's fluidic sample) interface.

It is another object of the present invention to provide a diagnostic test method that uses data processing techniques to identify electrical/electrochemical output data for quantifying the difference between patient and normal individuals and/or the difference between patient's at least two samples.

DETAILED DESCRIPTION OF THE EMBODIMENTS

A free (unbound) and/or bound FA level in a patient may be used to diagnose or monitor acute and chronic medical conditions. The method described here can be used as an indicator of presence, severity, activity, and staging of medical conditions during screening, at the initial diagnosis, in the treatment period and follow-up.

In one aspect, acute medical condition is acute myocardial ischemia in which an increased (up to 5-6) bound FA/albumin molar ratio (normal physiologic ratio is 0.2-1.5) and more than 2-3 fold increased free (unbound) FA level are observed in patient's blood sample immediately after the beginning of chest pain. Determination of albumin-FA complex (albumin occupied by FAs) to diagnose specific medical condition has been subject of the patent application publication no: US 2008/0305550 (Huff et al.). Determination of free FAs level has been subject of some other patents, like patent no: U.S. Pat. No. 6,750,030 (Kleinfeld et al.), and patent applications, like publication no: US 2011/0045520 (Bhagavan et al.), US 2002/0160537 (Kleinfeld A) and WO 2017/116358 (Oran I). The patent no: U.S. Pat. No. 9,354,222 (Jung B H et al.) disclosed usage of serum profile of multiple lysophosphatidylcholine and FA molecules in the diagnosis of acute myocardial ischemia. None of the patents or patent applications have disclosed the method described here.

In another aspect, acute medical condition is arterial or venous ischemia affecting various human organ, tissues or body parts which is characterized by increased free and/or bound (to albumin) blood FA levels; including, but not limited to, pulmonary embolism, preeclampsia, sepsis, stroke, carbon monoxide poisoning, deep vein thrombosis, lower and upper limb ischemia, intestinal ischemia, testicular torsion, hepatitis, liver failure, kidney failure, trauma related ischemia, placental ischemia and insufficiency in pregnancy, hypothermia, iatrogenic ischemia (i.e., organ harvesting for transplantation, ischemic preconditioning, remote ischemic preconditioning), post operative ischemia, exercise induced ischemia, ischemia with thrombolytic/fibrinolytic therapy, ischemia with thrombectomy, ischemia with reperfusion, ischemia with percutaneous transluminal angioplasty (PTA) and stenting.

In another aspect, chronic medical conditions are a series of congenital or acquired diseases, disorders or non-physiologic conditions which are characterized by primarily or secondarily altered FA metabolism accompanied by increased free and/or bound (to albumin) blood FA levels; including, but not limited to, fatty liver, steatohepatitis, chronic liver failure, cirrhosis, jaundice, chronic hepatitis, chronic renal failure, adiposity, obesity, metabolic syndrome, pancreatitis, polycystic ovary syndrome, mitochondrial fatty acid oxidation disorders, any medical conditions associated with mitochondrial dysfunctions, diabetes mellitus, cardiovascular disease, peripheral arterial disease, atherosclerosis, hypertension, any medical conditions with increased oxidative stress, like neurodegenerative diseases, rheumatologic diseases, premalignant and malignant diseases, and aging.

In a preferred embodiment, the method comprises: providing a sample from patient; adding the sample into the holder which contains at least two electrodes (one of them is made of carbon-based materials); incubating the sample within the holder in a predetermined period of time; thus, allowing most (if not all) sample's albumin molecules to face off carbon-based electrode surface. The rationale behind the preference of carbon-based electrode is the ability of carbon structure to perform "extraction-adsorption" processes. While the high surface area of carbon-based electrode leads to widespread contact between the albumin's FAs and the electrode, the carbon-based electrode begins to extract bound FAs from the albumin molecules. The extraction force is driven mainly by the hydrophobic interaction between the FAs and carbon-based electrode material. The extracted FAs constitute eventually a monolayer on the carbon-based electrode at the end of predetermined incubation period. After that, the sample's FA level can be determined by using an electrical/electrochemical measurement technique(s) which is(are) sensitive to ionic/molecular changes at the electrode-electrolyte (sample) interface. One such interfacial event is the formation of double layer capacitance. Finally, the electrical/electrochemical reading is interpreted whether measurement is indicative of acute or chronic medical conditions by comparing the results of normal individuals, patient's another sample, or patient's initial (at the beginning of incubation) and last (at the end of incubation) measurement.

There are two indispensable requirements of the said method; one is to maintain most (if not all) albumin molecules being in contact with carbon-based electrode surface, and another is to give sufficient incubation time which allows self-extraction of considerable amount of FA molecules from the albumin surface with subsequent transfer onto the carbon-based electrode. The contemporary well-known devices/techniques can be used to ensure these requirements. In one embodiment, if we have a sample in a milliliter quantity, the test can be done in a test cell (i.e., holder) with magnetic stirring bar in which most (if not all) albumin molecules can face off carbon-based electrode by stirring effect during incubation period. In another embodiment, if we have a sample in a microliter quantity, the test can be done in a flowing microfluidic system in which slowly flowing sample within the shallow channels (i.e., holder) allows most (if not all) sample's albumin to face off carbon-based electrode. In one another embodiment, if we again have a sample in a microliter quantity (e.g., one droplet), the test can be done over a flat surface (i.e., as holder), in which relatively wide electrode surface area and thin layer of sample spreading over the electrode area together allow most (if not all) sample's albumin to face off carbon-based electrode during incubation period. The screen-printed electrode system is an example of the latter. However, all other devices/techniques providing said two requirements known to those having skill in the science can be selected.

The method disclosed herein can be used alone, or in conjunction with other diagnostic tests to improve the accuracy and specificity of the diagnosis. These include commonly used myocardial injury biomarkers like cTnI, cTnT, myoglobin, CK-MB, fatty acid binding protein, IMA. The method can also be used for screening purpose, to identify individuals who appear to be "at risk" for further testing by this or other means.

The subject sample may be selected, for example, from the group consisting of whole blood, plasma, serum, urine, saliva, cerebrospinal fluid, sweat or other body fluids containing albumin and fatty acids. Preferably, the sample is blood. To improve accuracy, two or more samples may be tested concomitantly, consecutively, or intermittently.

The specific/working electrode consists of carbon-based materials. Examples are charcoal, activated carbon, carbon black, glassy carbon, regular graphite, highly oriented pyrolytic graphite, pencil graphite, graphite oxide, reduced graphite, graphene nanoparticle (nanosheets, nanotubes, nanoribbons, quantum dots), graphene oxide nanoparticle, reduced graphene nanoparticle, doped graphite/graphene with group I-III atoms (such as P, N, S, Si, B, K), graphite intercalation compounds (intercalated by but not limited to Li, K, Mg, Ca, Cl, Br, I, or combination), carbon nitride, graphane, graphone, fullerene, graphene nanoparticle decorated electrodes, metal (such as Pt, Fe, Ti, Au, Ag) decorated graphene/graphite, but all other carbon-based material or their combination capable of functioning as electrode known to those having skill in the science can be selected.

The electrochemical measurement technique which is sensitive to ionic/molecular changes at the electrode-electrolyte interface (e.g., double layer capacitance) includes square wave voltammetry, chronoamperometry, stripping voltammetry, electrochemical impedance spectroscopy, but all other electrical/electrochemical techniques known to those having skill in the science can be selected.

What is claimed is:

1. A method for extraction and determination of fatty acids in a biological fluid sample containing albumin, comprising the following steps;
    adding the biological fluid sample of a patient into a holder containing at least two electrodes, wherein one electrode of the electrodes is a carbon-based electrode with a high surface area,
    performing an incubation of the biological fluid sample in the holder in a predetermined period to increase a contact probability between the albumin in the biological fluid sample and the carbon-based electrode,
    performing an extraction-adsorption process during the incubation, wherein the extraction-adsorption process comprises an concomitant self-extraction of the fatty acids from the albumin and an adsorption of the fatty acids extracted onto a surface of the carbon-based electrode, due to a hydrophobic interaction between the fatty acids and a material of the carbon-based electrode,
    changing an electrode-electrolyte interfacial construct, while the extraction-adsorption process creates a layer of the fatty acids on the carbon-based electrode, wherein as the extraction-adsorption process goes, the electrode-electrolyte interfacial construct changes to form an electrical double layer,
    obtaining data with an electrical/electrochemical technique sensitive to changes of the electrode-electrolyte interfacial construct, wherein the changes of the electrode-electrolyte interfacial construct reflect a magnitude of the fatty acids extracted from the albumin,
    interpretating results from the electrical/electrochemical technique by comparing initial data of a normal individual and/or the patient at a beginning of the incubation with last data of the normal individual and/or the patient at an end of the incubation.

* * * * *